United States Patent [19]

Alexander

[11] Patent Number: 5,318,573
[45] Date of Patent: Jun. 7, 1994

[54] DEVICE FOR ASSISTING CHILDBIRTH

[75] Inventor: Gary E. Alexander, Baton Rough, La.

[73] Assignee: Medisys Technologies, Inc., Baton Rough, La.

[21] Appl. No.: 36,560

[22] Filed: Mar. 25, 1993

Related U.S. Application Data

[63] Continuation-in-part of Ser. No. 982,016, Nov. 24, 1992, Pat. No. 5,217,467, which is a continuation of Ser. No. 851,068, Mar. 13, 1992, abandoned, which is a continuation-in-part of Ser. No. 522,592, May 14, 1990, Pat. No. 5,122,148.

[51] Int. Cl.$^5$ .............................................. A61B 17/42
[52] U.S. Cl. ....................................... 606/122; 606/1; 606/119; 606/121
[58] Field of Search .................. 606/1, 119, 121, 122

[56] References Cited

U.S. PATENT DOCUMENTS

| | | |
|---|---|---|
| 713,166 | 11/1902 | St. Cyr . |
| 1,690,942 | 11/1928 | Odell . |
| 1,782,814 | 11/1930 | Froehlic . |
| 3,139,886 | 7/1964 | Tallman et al. . |
| 3,550,595 | 12/1970 | Laufe . |
| 3,605,748 | 9/1971 | Salinas-Benavides . |
| 3,665,925 | 5/1972 | Dersookian . |
| 3,785,381 | 1/1974 | Lower et al. . |
| 3,789,849 | 2/1974 | Laufe et al. . |
| 4,875,482 | 10/1989 | Hariri et al. . |
| 4,997,391 | 7/1986 | Janko . |

FOREIGN PATENT DOCUMENTS

| | | |
|---|---|---|
| 2233840 | 7/1972 | Fed. Rep. of Germany . |
| 2925386 | 1/1981 | Fed. Rep. of Germany ...... 606/122 |
| WO8911253 | 11/1989 | France . |

Primary Examiner—Stephen C. Pellegrino
Assistant Examiner—Glenn Dawson
Attorney, Agent, or Firm—William David Kiesel; Robert C. Tucker; C. Dean Domingue

[57] ABSTRACT

A device to assist in removing a fetus from a woman's birth canal during childbirth including a pliable, elongated, hollow member sized to fit over the head of the fetus, collar means attached at one end of the member to restrict the opening of the hollow member at that end to the desired size and insertion means for inserting the elongated, hollow member over the head of the fetus.

12 Claims, 13 Drawing Sheets

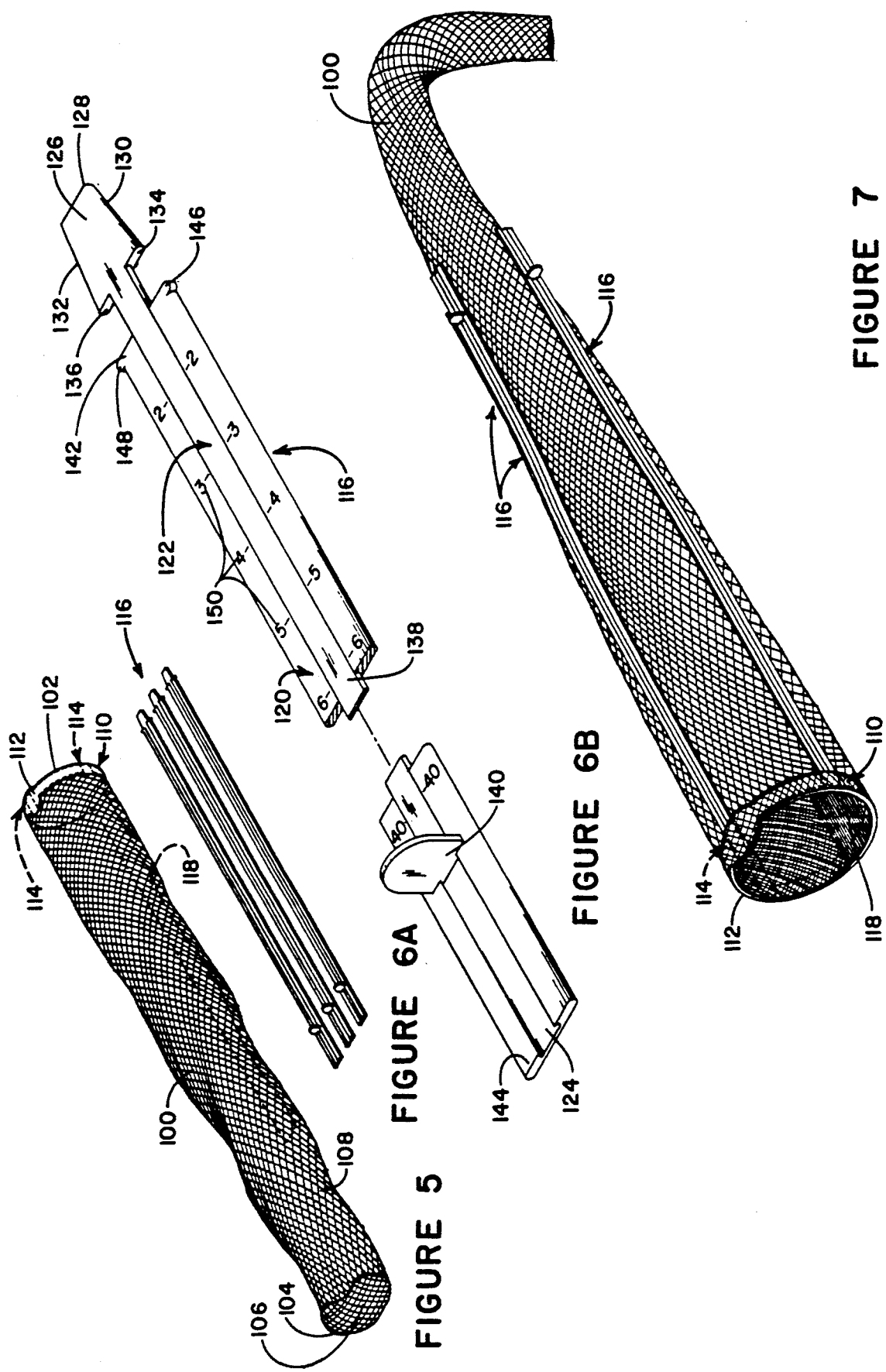

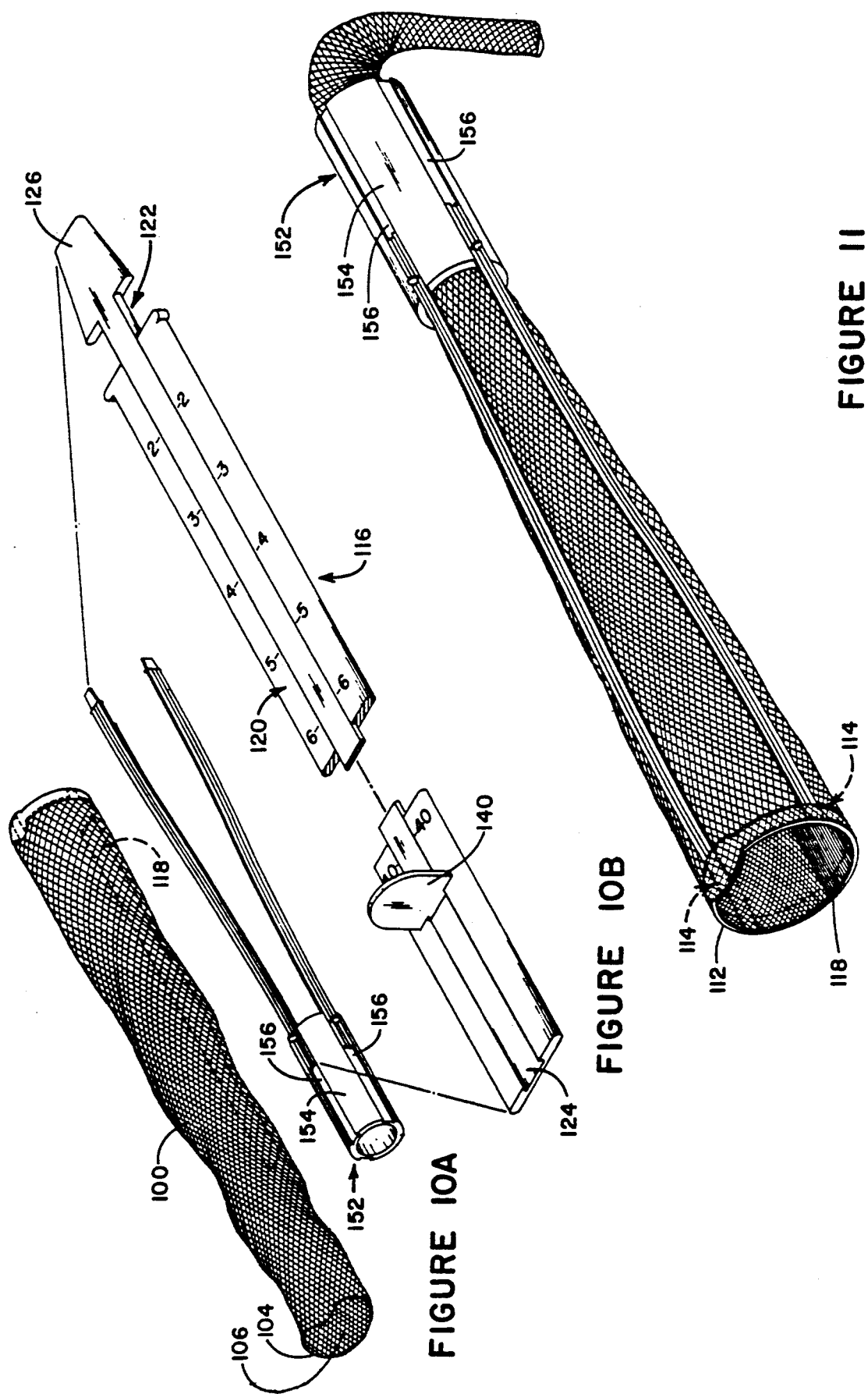

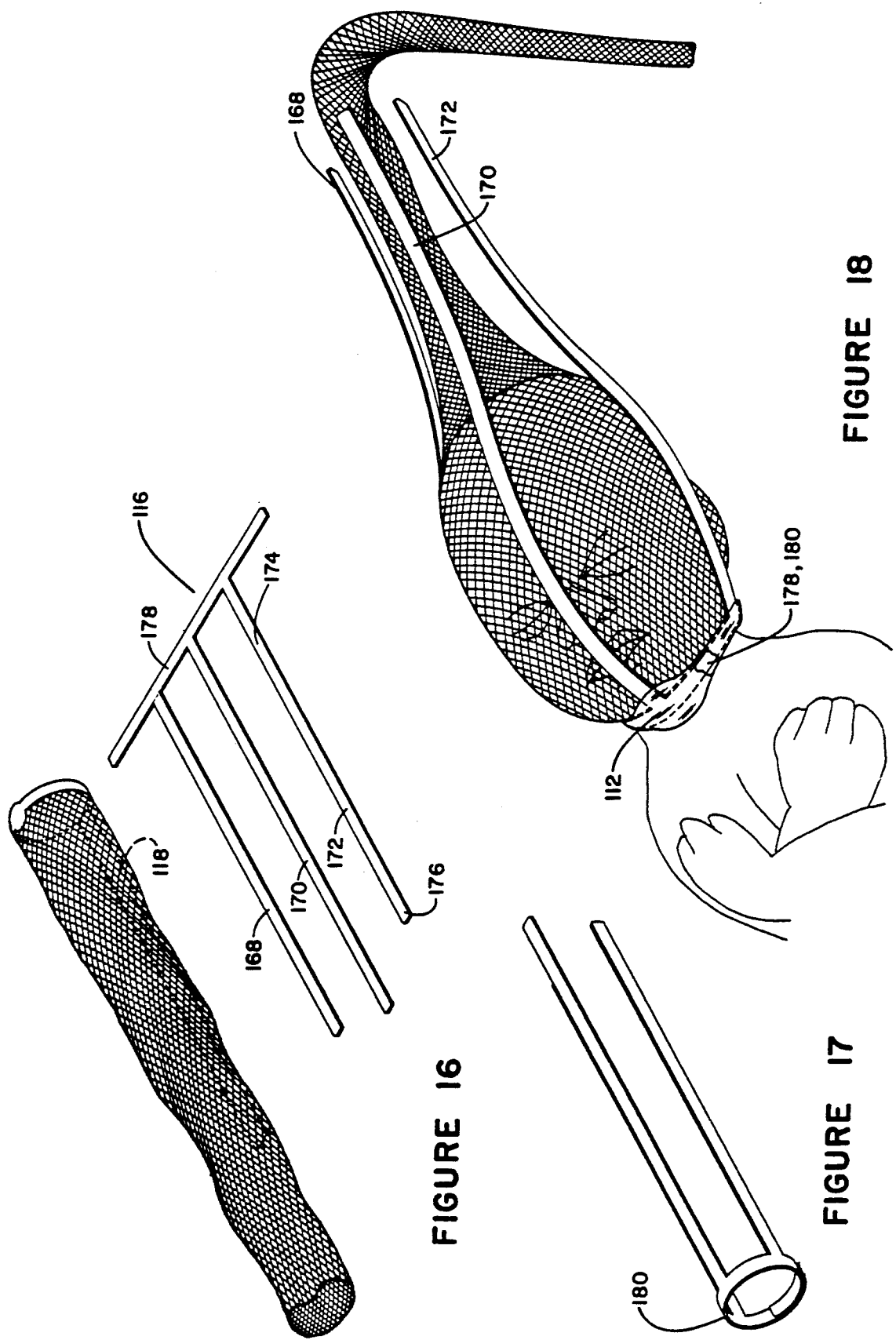

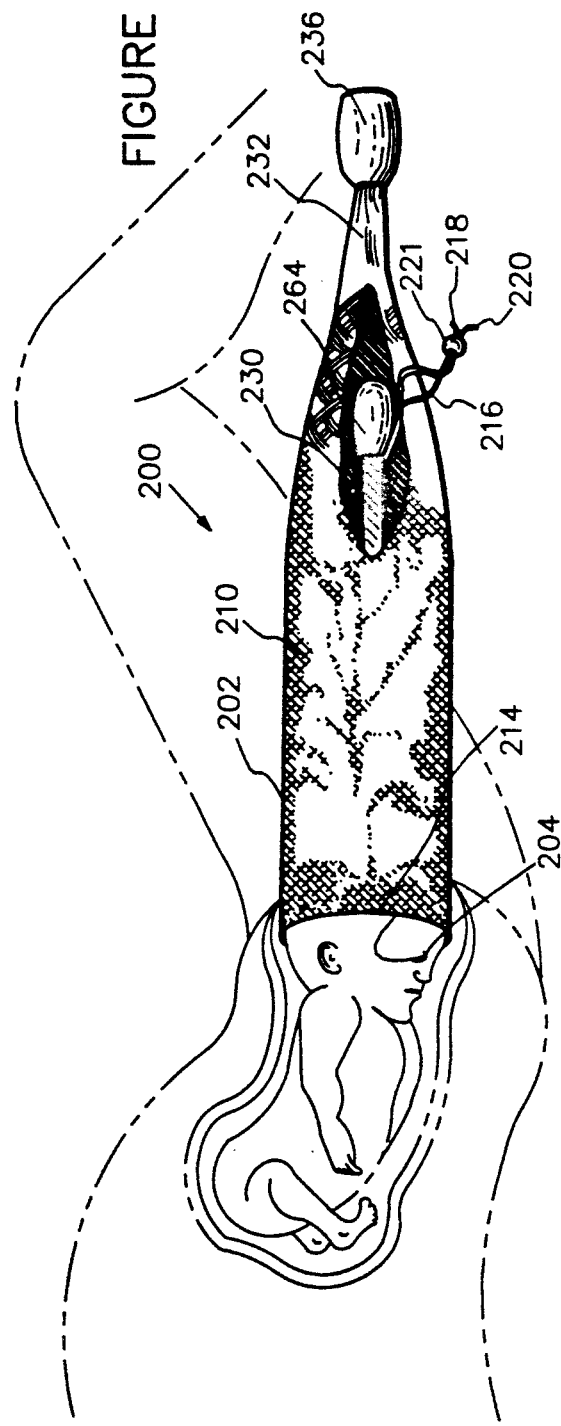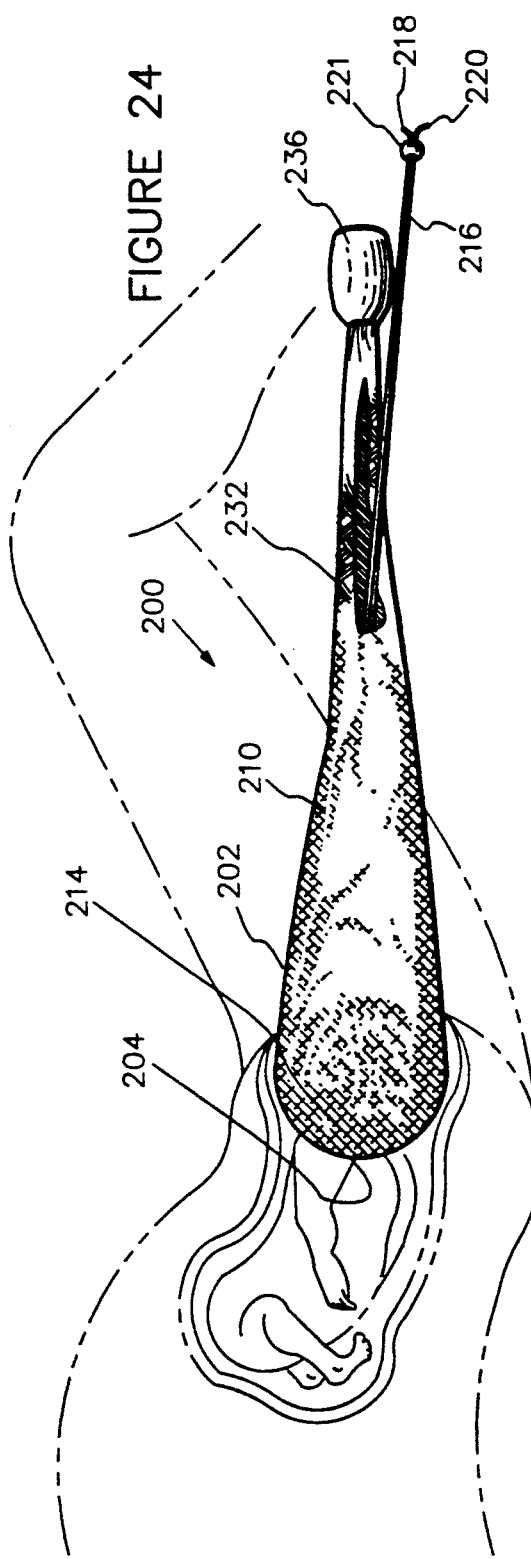

DEVICE FOR ASSISTING CHILDBIRTH

This is a continuation-in-part application of a copending U.S. patent application Ser. No. 07/982,016, filed on Nov. 24, 1992, now U.S. Pat. No. 5,217,467 which is a file wrapper continuing application of a copending U.S. patent application Ser. No. 07/851,068, filed on Mar. 13, 1992, now abandoned which was a continuation-in-part application of U.S. Pat. No. 5,122,148 filed May 14, 1990.

BACKGROUND OF THE INVENTION

1. Field of the Invention

This invention relates in general to obstetric devices, and more particular to devices useful in removing the baby during vaginal delivery.

2. Prior Art

Today's state of the art obstetrics utilizes various procedures to assist in instances of difficult vaginal deliveries. These procedures basically fall into three categories: version, Caesarian and forceps assisted delivery. In the case of severe cephalo-pelvic disproportion, placenta previa, vaso previa, and other contraindications to vaginal delivery, the "C-Section," whether classic or low transverse, remains the mainstay procedure. However, it has long been recognized that to the extent that C-Section deliveries can be successfully avoided, statistical maternal and fetal benefits will be realized. Even the non-difficult vaginal delivery can benefit from non-traumatic assists.

Many problems may develop during delivery which require assistance from the attending obstetrician to successfully remove the baby from the birth canal. One such problem results from the presenting part of the baby, usually its head, descending too slowly. This is particularly true in the case of the primigravida mother. Even with a completely dilated and effaced cervix, and an adequate pelvis, a fetus might refuse to descend beyond station "+1", especially when the mother is suffering from contraction exhaustion. This can remain a problem even with an assist from administration of oxytocin (Pitocin). This problem is frequently exacerbated by anesthesia, particularly in the instance of epidural anesthesia which frequently produces induced non-beneficial partial atony of the engaged and dedicated muscles. Such partial atony frequently results in non-beneficial, and sometimes hazardous, prolongation of labor. Station "+1" is considered mid-pelvis and in the usual case is considered too high for a forceps assisted delivery. The risks to the fetus with forceps application at this level are extreme. Forceps cannot be safely used until the presenting part is at least at station "+2", and preferably between stations "+2" and "+3", which is the floor of the perineum.

Modern obstetrics has not developed an alternative to the use of forceps when an assisted natural delivery is indicated, such as when the fetus is consistently exhibiting late decelerations of heartbeat following contractions or is exhibiting non-variability of the baseline heartbeat rate. Obstetrical forceps are typically, in their various types, two bladed affairs which are blindly inserted one blade at a time in a hopefully temporal-cheek position and then articulated together before assisting traction is applied. Actual traction is exerted slightly below or underneath the mandible. The traction is point concentrated and slippage of the forceps is increased because of natural lubrication, refusal of the fetal skull to conform to existing forceps design, and other known myriad of variables that vary from one fetus-to-pelvis physical relationship to another.

Even proper positioning of the forceps can result in harm to the fetus. For example, in instances of minimal cephalo-pelvic disproportion, the insertion of one blade of the forceps can exacerbate any slight deficiency in birth canal adequacy. In addition the softness, or pliability, of the fetal skull, coupled with the existence of sutures which separate the plates of the skull, render the skull susceptible to trauma associated with metal forceps assisted deliveries.

The problems associated with forceps assisted deliveries are well known, and many attempts have been made to improve forceps design. Examples of the current state of the art in forceps design can be seen in the following patents: U.S. Pat. No. 3,550,595 entitled "Obstetrical Forceps" and issued on Dec. 29, 1970 to Leonard E. Laufe; U.S. Pat. No. 3,605,748 entitled "Obstetrical Forceps" and issued on Sep. 20, 1971 to Hector Salinas-Benavides; U.S. Pat. No. 3,665,925 entitled "Obstetrical Forceps" and issued on May 30, 1972 to Hamo M. Dersookian; U.S. Pat. No. 3,785,381 entitled "Pressure Sensing Obstetrical Forceps" and issued on Jan. 15, 1974 to Brenton R. Lower et al; U.S. Pat. No. 3,789,849 entitled "Obstetrical Forceps" and issued on Feb. 5, 1974 to Leonard E. Laufe et al; and U.S. Pat. No. 3,794,044 entitled "Delivery Forceps" and issued on Feb. 26, 1974 to William O. Vennard.

Despite the long felt need and the large amount of time and effort spent to develop an alternative to forceps, the only assisting device developed which has seen some application is a vacuum extractor. Because of the difficulty in the safe use of this device, it has not proven to be successful and its use has in large measure been abandoned.

OBJECTS AND SUMMARY OF THE INVENTION

It is therefore an object of this invention to provide an assisting device for childbirth which can safely perform substantially all of the functions of forceps.

Another object of this invention is to provide an assisting device for childbirth that is easy to use and reduces the risk of injury to the fetus during childbirth.

Still another object of this invention is to provide an assisting device for childbirth that can be quickly applied to the skull of the fetus by the attending obstetrician.

Still another object of this invention is to provide an assisting device for childbirth that can be quickly applied to the lower portion of the fetus by the attending obstetrician in the case of a breech birth.

Still other objects and advantages of this invention shall become apparent from the ensuing descriptions of the invention.

BRIEF DESCRIPTION OF THE DRAWINGS

FIG. 5 is a three dimensional view of another embodiment of this invention.

FIG. 6A is a three dimensional view of one embodiment of the insertion means.

FIG. 6B is an enlarged view of the insertion means seen in FIG. 6A.

FIG. 7 is a three dimensional view of one embodiment of this invention which utilizes the insertion means of FIGS. 6A and 6B.

FIG. 10A is a three dimensional view of on the embodiments of the handle means of the invention.

FIG. 10B is an enlarged view of the insertion means which can be utilized with the aforementioned handle means.

FIG. 11 is another three dimensional view of one embodiment of the invention utilizing the handle means.

FIG. 16 depicts an alternate embodiment of the present invention.

FIG. 17 is another view of the embodiment seen in FIG. 16.

FIG. 18 is a three dimensional view of the embodiment seen in FIG. 17 attached to the head of the infant.

FIG. 23 is an illustrative view of the preferred embodiment of FIG. 20 being placed about the fetal head.

FIG. 24 is an illustrative view of the preferred embodiment of FIG. 20 as the device is in traction.

PREFERRED EMBODIMENTS OF THE INVENTION

Figure 1:
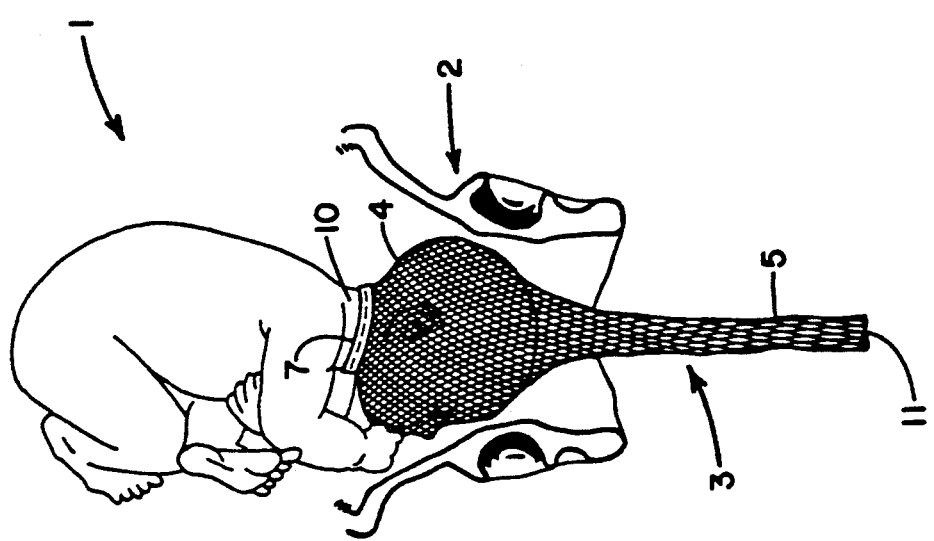
FIG. 1 is cutaway view of an unborn infant positioned for vaginal delivery to which has been attached one embodiment of this invention.

Like numbers in the various figures refer to like components from the specification. Referring now to FIG. 1 which depicts one embodiment of the present invention, a fetus, generally denoted by numeral 1, is depicted positioned in a cutaway of a portion of a woman's birth canal 2 having the childbirth assist device 3 attached to its head 4 and trailing outside of the vagina area of the birth canal 2.

Figure 2:
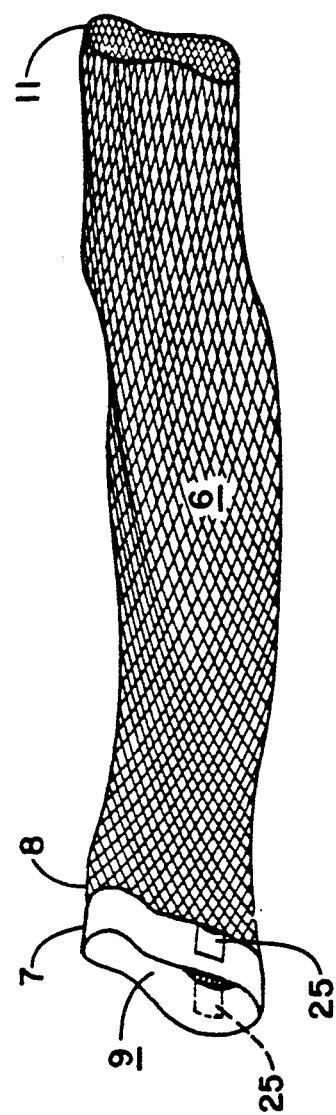
FIG. 2 is a three dimensional view of one embodiment of this invention.

In its broadest context as shown in FIG. 2, the device 3 comprises an elongated sock-like member 5 open at both ends not only to allow a physician to fit his hand and arm in passageway 6 of member 5 for rotational purposes, but also to allow the head 4 to fit into passageway 6. In addition device 3 comprises a collar 7 attached at one end 8 of member 5 which can be adjusted to restrict the size of opening 9 formed at end 8.

In one embodiment, member 5 is constructed from material having some elasticity characteristics, and more preferably from a material selected from a group consisting of natural fibers or manmade plastic fibers. Natural fibers could include cotton, linen and silk. Plastic fibers could include nylon, dacron and rayon. Preferably the degree of elasticity should be at least to a degree such that the material would begin to stretch before the pulling force exceeded a predetermined amount. That amount would depend on the stage of development of the fetus, as well as other known factors. The degree of elasticity is preferably set so the pulling force is less than that which would harm the fetus. Member 5 is also preferably pliable so that it can be shaped and easily moved in position about head 4. In another preferred embodiment the material will be constructed from a mesh material, the size of the mesh would preferably be sufficiently small enough to reduce chances of non-beneficial oral ingestion of toxic meconium by the fetus. In still another preferred embodiment the fabrics would be sterilized and lubricated with K-Y jelly to reduce or prevent the fabric from absorbing the natural lubricants within the womb. K-Y jelly is a brand name for a product sold by Johnson & Johnson.

Figure 4:
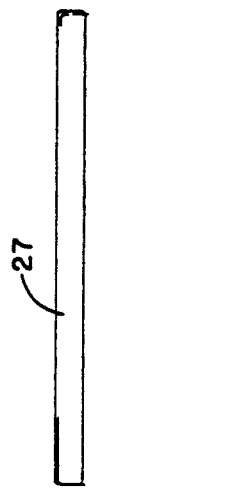
FIG. 4 is an enlarged view of another embodiment of the closure means forming part of this invention.

The member 5, which in one embodiment will be constructed of the aforementioned mesh material, will comprise an angular mesh as seen at 5 of FIG. 4. Once the member 5 has been placed in position over the head of the infant, this angular mesh will impart a uniform distribution of forces, as in the manner of the Chinese handcuff, as the member 5 is pulled in a linear direction, with respect to the passageway 6. In other words, all areas of the infants head which are in contact with the mesh of member 5 will have exerted against it a gripping axial force created by the diminishment of size of the angular mesh secondary to traction; thus, as the member 5 is pulled, all of the pulling force will be distributed across the area which is in contact with the infant's head and axial gripping of the child's head has been initiated. Also, in one embodiment, the angular mesh is constructed of a synthetic or natural fiber. The fiber can be round or elliptical in cross-section and be mono-filament or bi-filament fibers.

In the embodiment shown in FIG. 2, collar 7 is constructed of an elastic material which can be stretched to fit about head 4 and then will contract to an extent to fit loosely about the neck area 10 of the fetus 1. In this manner collar 7 will not choke the fetus 1, but also will not easily slip over the head 4 when the physician pulls on end 11 of member 5 during the delivery process as described below.

Figure 3:
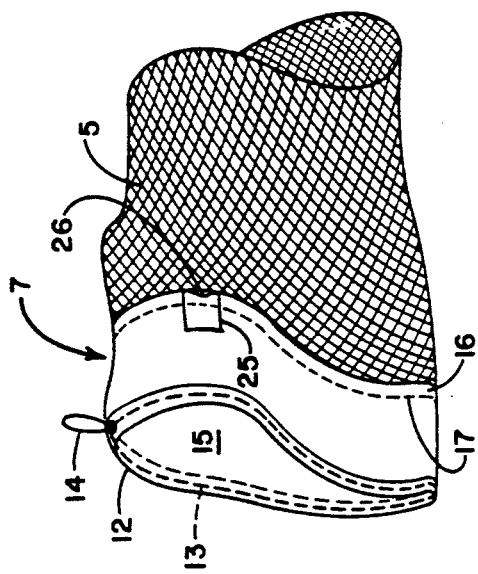
FIG. 3 is an enlarged view of one embodiment of the closure means forming part of this invention.

In another embodiment as shown in FIG. 3, collar 7 is constructed from a pliable material wherein one edge section 12 has been folded over and stitched to itself to form a drawstring pocket 13 in which drawstring 14 has been placed. When drawstring 14 is pulled opening 15 is restricted. The other edge section 16 of collar 7 is stitched or otherwise connected to member 5 along line 17.

In a third embodiment as shown in FIG. 4, collar 7 is constructed of a strip 18 of pliable material having one section 19 stitched or otherwise connected substantially about the perimeter of end 8, and having another section 20 that can extend over a portion of the first section 19. Strips 21 of Velcro or similar material are attached to side 22 of section 19 in a position to be alignable with at least a portion of the strips 23 of Velcro or similar material attached to side 24 of section 20. Velcro is a registered trademark of VELCRO INDUSTRIES, B.V. (NETHERLANDS CORPORATION) identifying hook and loop fastener systems. The size of opening 15 can be adjusted by changing the alignment of the strips 21 and 23. Opening size is then maintained by contacting the overlapping sections of the strips to one another.

In the embodiment as illustrated in FIGS. 2-4, collar 7 is provided with one or more pockets, preferably two or more, formed by a piece 25 of fabric that is attached on three sides to collar 7 to form an opening 26 facing toward member 5. The opening 26 will be large enough so that one end of wand 27 can be inserted through the opening. Wand 27 is preferably constructed from a flexible material, such as plastic, that would will allow it to conform to the shape of the fetus' head, yet rigid enough to allow it to be used to push collar 7 around the fetus' head when positioning device 3.

Figure 8:
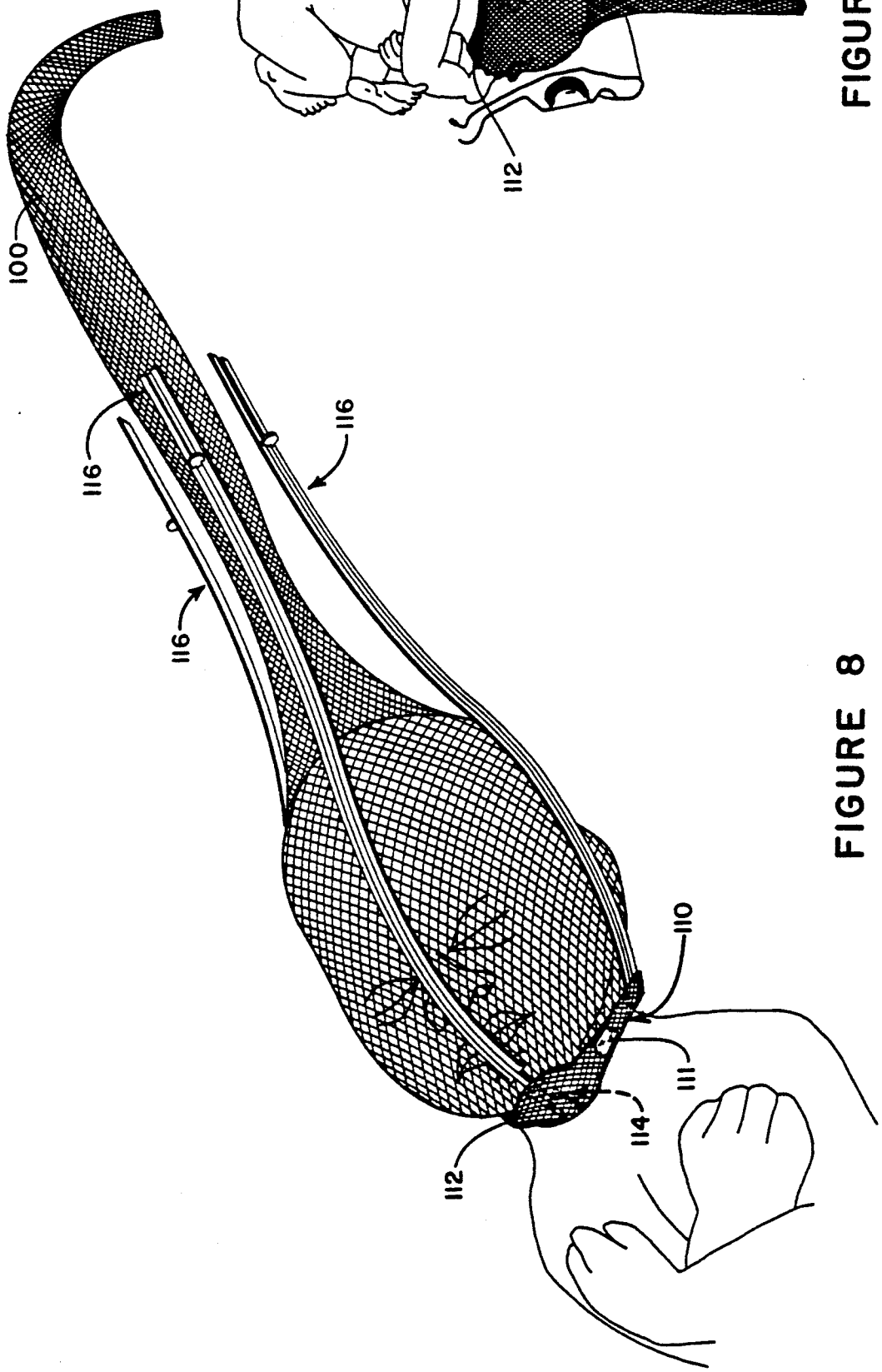
FIG. 8 is a three dimensional view of the unborn infant to which the embodiment, as seen in FIG. 7, has been attached.

Referring to FIG. 5, another embodiment of the present invention is depicted. The elongated member 100 has a first end 102 and a second end 104, with a passageway 106 defined therein. The member is constructed of the angular mesh material 108, as previously described. The collar means 110 is constructed of pliable material and is similar in design to the collar 7 in that collar 110 is connected to the first end 102 of the elongated member 100, so that the first end 102 encircles the infant's neck. The collar means 110 will have an elastic band 111, as seen in FIG. 8, sewn into the hem of the collar and sized to rest at a diameter sufficient to preclude carotid or larynx compression and to expand to a diameter sufficient to permit application over the largest portion of the fetal skull.

The collar means 110 will also contain a widened below chin segment 112, which is also illustrated in FIG. 7. The chin segment 112 is generally a protuberance on the collar means 110 which is adapted so that the infants chin can be abutted adjacent thereto when the member 100 is being pulled during childbirth. The collar means 110 will also comprise pocket means 114, similar to the aforementioned pockets 25, for receiving the wand or wands 116, which is also referred to as the insertion means 116, as seen in FIG. 6A.

The elongated member 100 can also posteriorly contain a linear mesh segment 118 which is attached to the first end 102 and is best seen in FIG. 7. The linear mesh segment 114 will exhibit enhanced tensile properties so that during delivery, the fetus' skull may be tilted in a vertical plane relative to the sternum by applying traction to the linear mesh segment 114 to achieve increased flexion.

Figure 19:
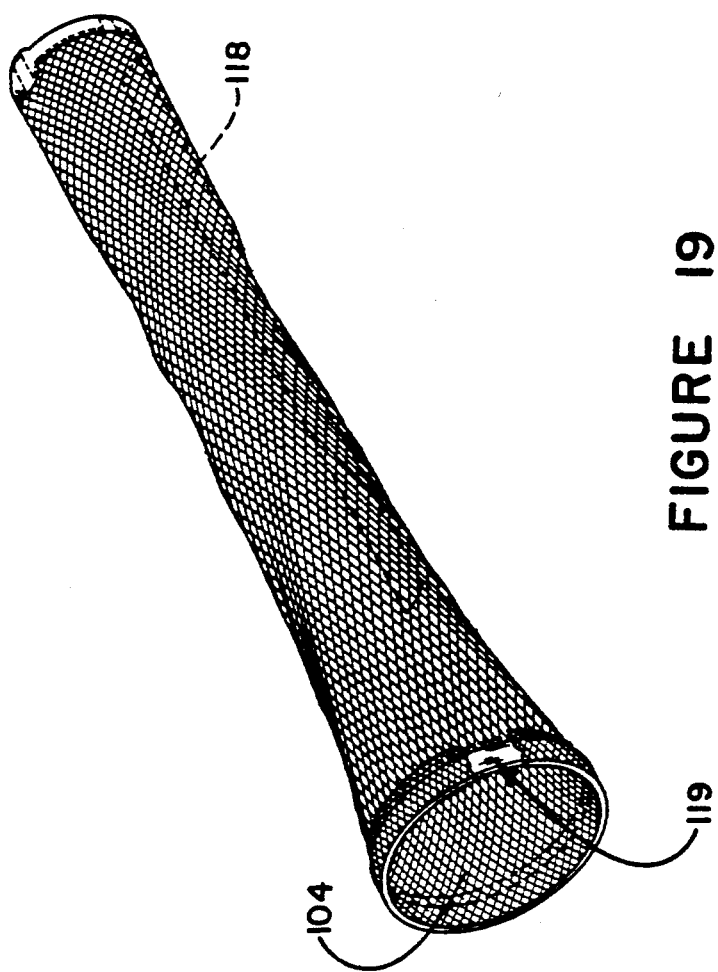
FIG. 19 is a three dimensional view of another embodiment of the invention.

As seen in FIG. 19, the second end 104 can contain an access means 119, which is a rigid, plastic ring of an internal diameter equal to or slightly larger than the internal diameter of the passageway 106. The access means will permit the immediate access through the cylinder to the fetal skull for usual and necessary obstetrical procedures.

Referring to FIG. 6A and 6B, one embodiment of the insertion means will now be described. The insertion means 116, or wand 27 as referred to earlier in this application, is provided for inserting the collar means 110 over the infant's head. The insertion means, as seen in FIGS. 6A and 6B, will have a first and second member 120, and 122. The second member 122 will overlay the first member 120 in the slotted groove 124 of member 120.

Member 120 will have a first end wedge section 126, with said wedge section having a first surface 128 which extends to angled shoulders 130 and 132. Shoulder 130 terminates at the back surface 134 and shoulder 132 terminates at the back surface 136. Both surfaces 134 and 136 extend to the elongated segment 138, with the elongated segment extending to the perpendicular segment 140, also known as the thumb tab.

The elongated segment 138 is slidably disposed within the groove 124 of the first member 120 so that the segment may be moved outward or inward in a telescopic fashion. Thus, if the operator is holding first member 120, and exerts a force on the thumb tab 140, the second member will be moved away relative to the first member 120.

First member 120 will have a first and second end 142, 144, with the first end containing ridges 146 and 148. Ridges 146 and 148 will be sized so that as the ridges are placed within the pockets 112, the ridges 146 and 148 engage the pocket with some mechanical restriction. First member will also have defined thereon graduations 150, marked in centimeters.

Referring now to FIG. 7, the insertion means 116 have been inserted into the pocket means 114 before the apparatus is attached to the fetus. In this position, the ridges 148 and 146 are fitted into pocket 112 with some mechanical restriction so that the ridges do not easily slip out of the pockets during positioning of the apparatus. In FIG. 8, the invention is attached to the infant's head. Hence, utilizing the insertion means 116, it can be seen that the collar means 110 has been positioned around the infants neck and the chin segment 112 has been placed beneath the mandible area. The elastic 111 of the collar means 110 will, therefore, cause the collar to surround the neck so that the elongated member 100 does not slip off.

After the proper position has been obtained about the fetus, the insertion means 116 can be removed from the pockets 114 as seen in FIG. 8. This will entail the physician having to hold member 120, then begin pushing second member 122 by pushing on the thumb tab 140 in a direction such that surface 128 is constrained against the pocket means 114. This will cause the wedge member 126 to continue to act against the pocket member 112 and thereby cause the collar means to move, but because the member 120 is being held stationary, the ridges 146 and 148 will be slipped out of the pocket 112. Conversely, the physician can hold the thumb tab 140 stationary, and pull on the first member 120 thereby disengaging the ridges 146 and 148 from the pockets.

Figure 9:
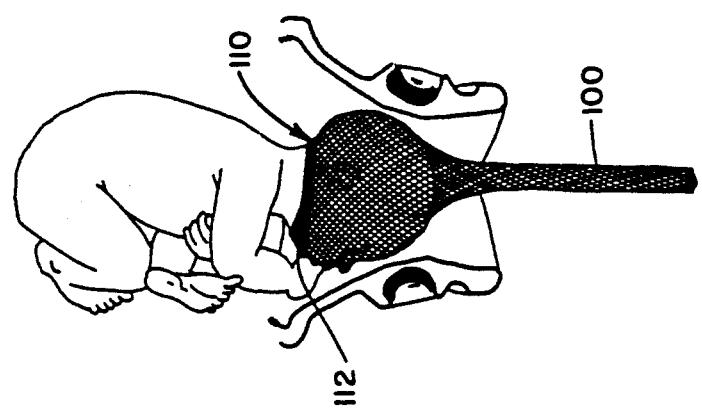
FIG. 9 is a cut-away view of an unborn infant positioned for vaginal delivery utilizing another embodiment of the invention.

FIG. 9 shows a cut-away view of the infant in the birth canal after placement of the collar means 110 in the position for removal of the infant. As can be seen from this view, the chin segment 112 is centered below the mandible. As noted earlier, as the elongated member 100 is pulled by the operator of the device, which in most cases is a medical doctor, the axial gripping forces of the mesh will distribute the pulling forces to all areas of the mesh which have been expanded by the infant's head.

Referring to FIG. 10A and 10B, handle means 152 is shown which may be used for holding and placing the aforementioned insertion means 116 into the pocket means 114. The handle means comprises generally a tubular cylinder 154 which has an internal diameter roughly the size of the passageway 106. The cylinder 154 will contain a plurality of slots 156 which will have fitted therein the first member 120 of the insertion means 116. In particular, second end 122 will be inserted into one of the slots 156. In the preferred embodiment of the handle means 152, there will be three slots, such that three wands 116 can be attached to the handle means 152.

As seen in FIG. 11, the handle means 152 has been attached to the elongated member 100 by placing the second end 144 of wands 116 into the slots 156, and by having the wedge section 126 of the second member 122 engaged with the pocket means 114. As seen in FIG. 11, the apparatus, which includes the handle means 152 containing the insertion means 116 is now available for placement over the fetal head.

Figure 12:
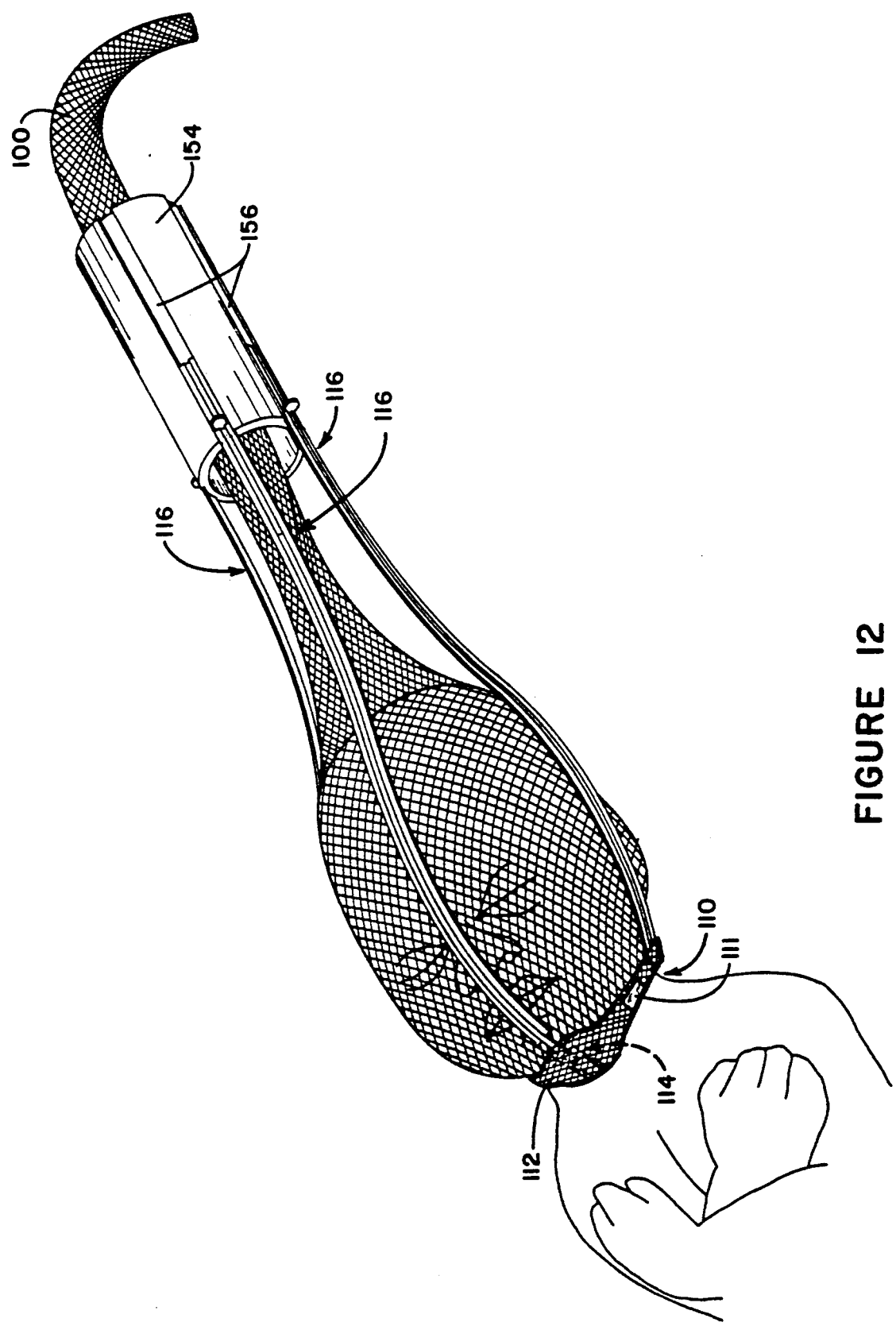
FIG. 12 is a three dimensional view of the handle means being utilized to position one embodiment of the present invention over the head of the infant.

In order to remove the handle means 152, disengagement of the wands 116 with the pocket means is accomplished as previously discussed. FIG. 12 shows the position of the handle means 152 after the apparatus has been placed over the head of the fetus and removal of the insertion means has begun. FIG. 12 also shows the elastic band 111 of the collar means 110.

Figure 13:
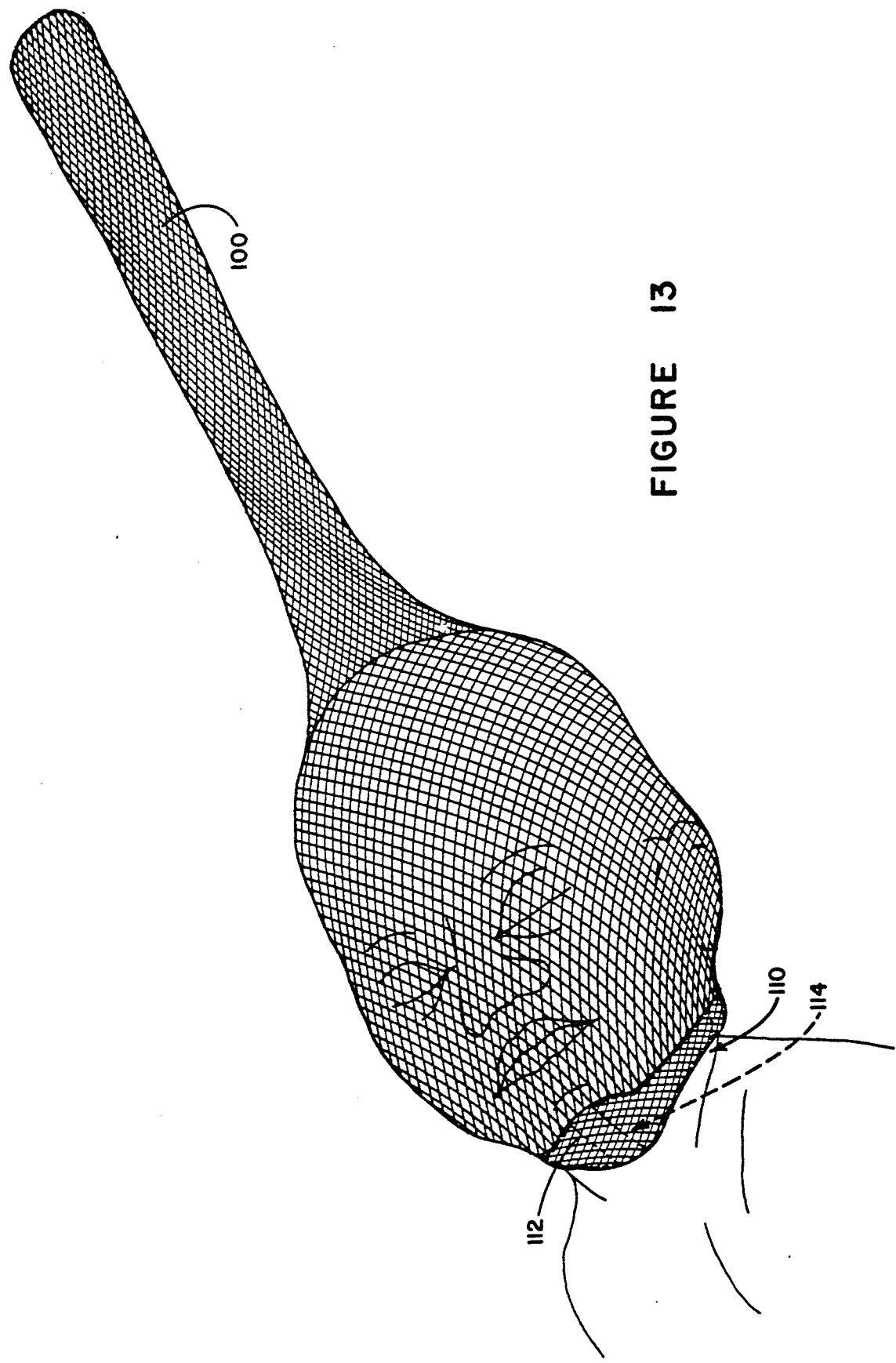
FIG. 13 is a three dimensional view of the another embodiment of the present invention attached to the head of the infant.

Turning to FIG. 13, the elongated member 100, along with the collar means 110 and chin segment 112, is shown after the insertion means 116 have been removed. As can be seen, the angular mesh has been expanded by the head of the infant so that the previously described axial gripping force will be applied once the doctor has exerted a lateral pull on member 100 to assist in the removal of the infant from the birth canal.

Figures 14A, 14B, 15:
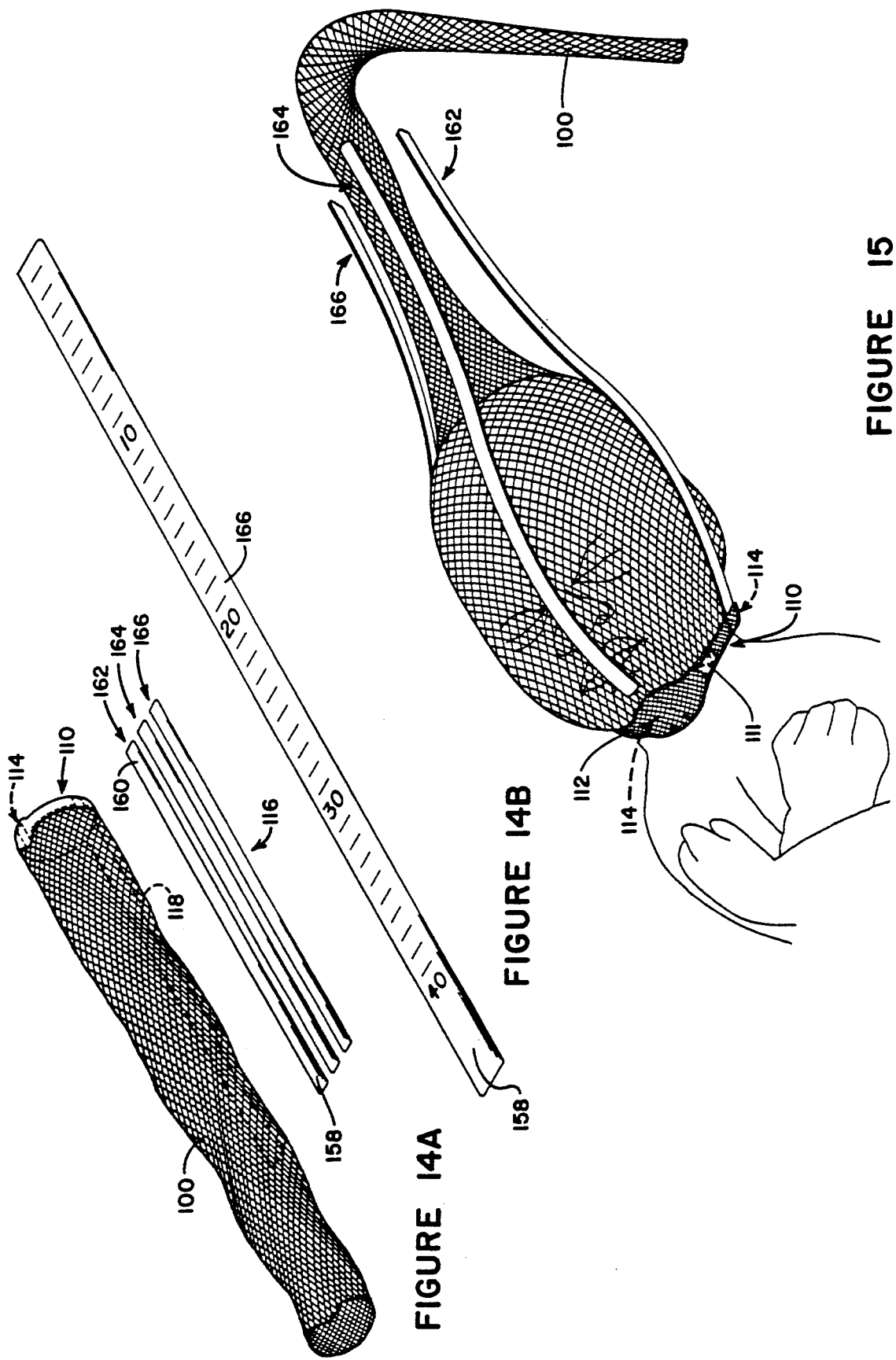
FIG. 14A depicts a plurality of the insertion means utilized with the embodiment of FIG. 13.
FIG. 14B is an enlarged view of one of the insertion means as seen in 14A.
FIG. 15 is a three dimensional view of the embodiment depicted in FIG. 13.

Referring now to FIGS. 14 and 15, another embodiment of the present invention will be discussed. The insertion means 116 consist of a single, flat, one-piece flexible wand with a first end 158 and second end 160. In the embodiments of FIGS. 14 and 15, three flexible wands will be employed, 162, 164 and 166. The single wands, 162, 164 and 166, will have already been placed within the pockets 114 which are disposed about the collar means 110 before the apparatus is placed over the fetal head.

FIG. 14B shows an enlarged view of the wand 166, with graduations in centimeters. The first end 158 will fit with some mechanical constriction into the pocket means 114, as can also be seen in FIG. 15. Thus, as shown in FIG. 15, the wands 162, 164, and 166 are positioned within the pockets 114 of collar 110. The first end 158 of wand 164 is illustrated as being pulled away from the collar means 110. In other words, the wand 164 has been pushed downward into the proper below mandible position by manipulating the wand downward. Next, wands 162 and 166 are manipulated, and once the proper position is reached, the wands 162, 164, and 166 can be removed by pulling the wands away from the pockets, which is shown by the relative position of wand 164 to the collar means 110.

FIG. 16 depicts another embodiment of the insertion means 116. In this embodiment, three elongated, flat, elongated wands 168, 170 and 172. Each of these wands will have a first end 174 and a second end 176, with the first end 174 of the wands 168, 170 and 172 being joined to a perpendicular member 178 which forms a collar 180, as seen in FIG. 17. In this embodiment, the perpendicular member 178 will be fitted into a folded latex hem of the woven mesh cylinder. The internal diameter of collar 180 at rest will be sufficient to preclude compression of the carotids or of the larynx and with an expansion diameter sufficient to permit application over the fetal skull. FIG. 18 shows the member 178 in place, as the member 178 has been folded to form a collar 180.

Figure 20:
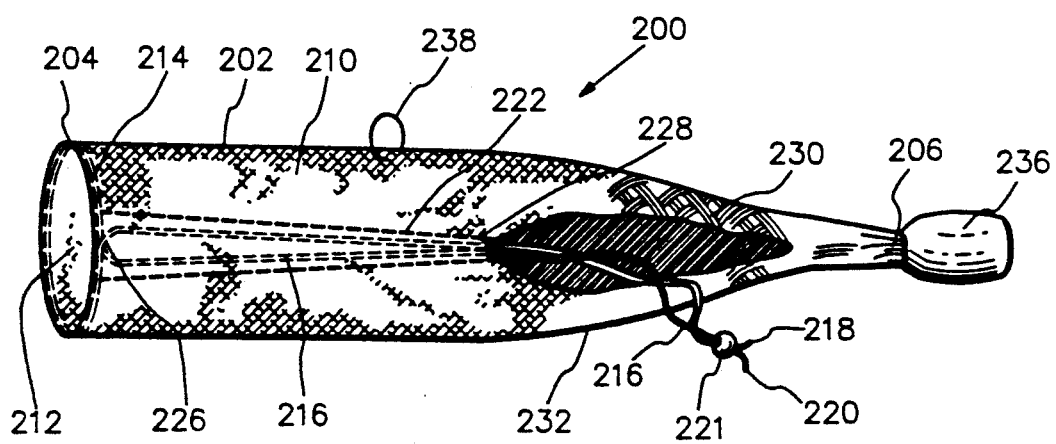
FIG. 20 is a three dimensional view of the preferred embodiment of the invention.
Figure 22:
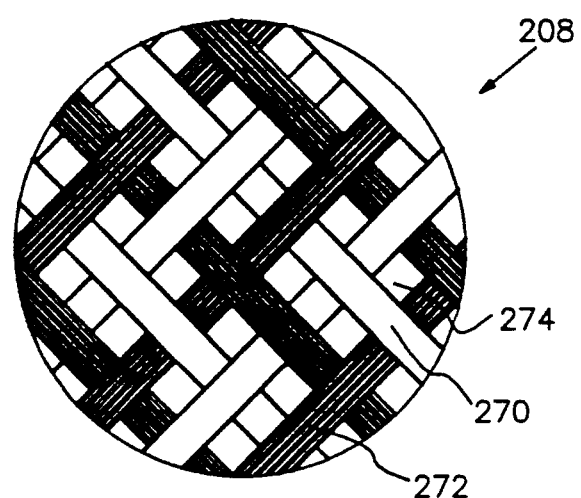
FIG. 22 is an enlarged segment of the angular mesh material of the preferred embodiment illustrated in FIG. 20.

Referring to FIG. 20, the preferred embodiment of this invention will now be described. The device for assisting delivery, seen generally at 200, comprises a cylindrical member 202 having a tubular passageway, the cylindrical member including a first end 204 and a second end 206. The cylindrical member 202 will be formed of an angular mesh material 208, also known as a braid, that is seen in FIG. 22 and will be more fully set out later in this application.

The angular mesh material 208 is formed similar to the other angular mesh material of the other disclosed embodiments so that as the cylindrical member 202 is pulled by the operator of the device, the axial gripping forces of the mesh will distribute the pulling forces to all areas of the mesh which have been expanded by the infant's head.

The cylindrical member 202 will have a first outer layer 210 and a second inner layer 212. As depicted in FIG. 20, one way to obtain this first 210 and second 212 layered cylindrical member 202 is to extrude a continuous cylindrical member, and then, fold the cylindrical member so that a first outer layer 210 and a second inner layer 212 is formed.

Once the cylindrical member has been folded over, a first end 204 is formed. The collar means 214 for encircling the neck of the fetus is generally located within the first end 204. The collar means 214 will be an enveloping structure such as a nylon sheath member that will contain a drawstring 216. The drawstring 216 will have a first end 218 and a second end 220 and is held together by fastener 221. As can be seen in FIG. 20, the drawstring is looped around the end portion 204 within the collar means 214 of the cylindrical member 202 such that the looped portion of the drawstring 216 constitutes part of the collar means 214. Thus, as the drawstring 216 is pulled, generally from the fastener 221, the looped portion of the drawstring 216 will decrease in size, which in turn will cause the diameter of the collar means 214 to decrease.

Figure 21:
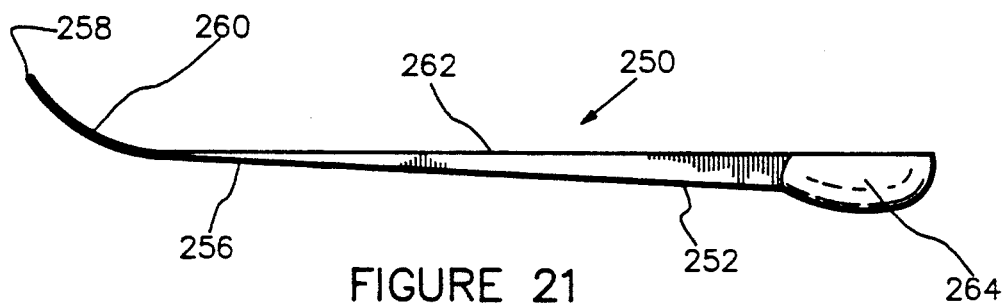
FIG. 21 is a two dimensional view of the insertion wand member used with the preferred embodiment illustrated in FIG. 20.

A sheath 222 which is positioned between the outer layer 212 and the inner layer 212 is also provided. The drawstring 216 can be held within the sheath 222 as seen in FIG. 20. A second sheath positioned approximately 180 degrees from the first sheath 222 may also be provided but has not been shown. The sheath is generally an elongated nylon pocket member that is adapted to receive the insertion wand member 250 as seen in FIG. 21, and as will be described in further detail.

The sheath 222 will be attached at two different points to the device 200. First, the sheath 222 will be attached to the first end 204 at 226 of the cylindrical member. Second, the sheath 222 will be attached to the cylindrical member at point 228. The point of attachment 228 is generally the point wherein the cylindrical mesh material member is no longer woven, which is referred to as the beginning of the pigtails. Further, at each attached point 226 and 228, the sheaths 222 are attached only to one wall of the device 200. This prevents interruption of inability to peel and compress in the event the device will need to be removed before delivery of the fetus.

As seen in FIG. 20, the point wherein the cylindrical member is no longer woven then branches out until three different pigtail branches 230, 232, 234. These branches 230, 232, and 234 will then be joined together at handle means 236. The traction handle means 236 are used to hold the different branches of material together, as well as being used as a location for the operator of the device, generally a medical doctor, to grab hold and exert a lateral pulling force thereon. As seen, the handle means 236 is an oval shaped member, but of course may take on different shapes.

Removal ring means 238 are also provided. The ring means 238 are for quick removal of the device if necessary. The ring means 238 are attached only to the outer layer 210. The ring means 238 functions by allowing pulling to be done only on the outer wall 210 of the cylinder 202 on one quadrant. Pulling on the ring means 238 by the operator causes the cylinder to peel off of the fetus' head by destroying the axial gripping of the angular mesh 208. The ring means 238 must be positioned on the cylinder 202 such that they remain outside of the introitus for easy access after application of the device 200.

Referring now to FIG. 21, the cephalic curve insertion wand member 250 of the preferred embodiment is illustrated. The insertion wand member 250 has a first surface 252 that in turn leads to a first angled surface 254, with angled surface 254 concluding at second angled surface 256. The second angled surface 256 terminates at end 258. The end 258 can be flattened (not shown) to prevent protrusion through the webbing during application. Extending from the end 258 is the curved surface 260 which generally approximates the cephalic curve of the fetus. The curved surface extends to the surface 262, with surface 262 concluding at the wand insertion member handle means 264. Wand end 258 must be thin enough to be pliable, yet thick enough to retain longitudinal strength.

Referring now to FIG. 22, the angular mesh braid material 208 will now be described. Generally, the angular mesh braid iteration 208 will be made up of two alternating materials. A flat shoe string material 270 will be interwoven with a series of multiple monofilament strands 272, such as fishing line. This composition gives body to the device 200, enhances axial gripping and adds strength to the angular mesh material 208. In the preferred embodiment the number of monofilament strands used in series is six. It should be noted that the portion of angular mesh material 208 depicted in FIG. 22 pertains to both the outer layer 210 or inner layer 212.

Figure 25:
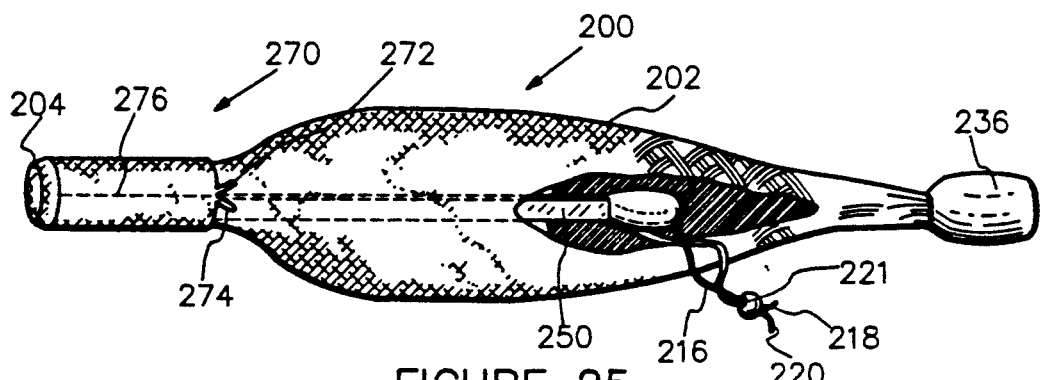
FIG. 25 is a three dimensional view of the preferred embodiment of FIG. 20 that has contained thereon the shrink wrap means.

Referring to FIG. 25, the preferred embodiment is depicted wherein a shrink wrap means 270 is included. The shrink wrap means 270 is generally a cylindrical piece of clear plastic which is disposed about the end 204. The shrink wrap means 270 is included in order to constrict the diameter of the first end 204 so that the device 200 can be inserted to a sufficient depth, and then once the appropriate depth is reached, which generally is about one-half inch into the vaginal introitus, but may vary depending on the characteristics of the mother, the tabs 272, 274 will be pulled by the operator of the device and the device will be separated along the perforated line 276. Next, the shrink wrap means is then removed and discarded. Since the end 204 has been inserted to a sufficient depth, the device 200 is in place to begin positioning the collar means 214 about the head of the fetus as will be more fully set out in the operation portion. FIG. 25 also depicts the insertion wand member 250 which has been inserted into the sheath member 222, as well as the draw string 216.

Figure 26:
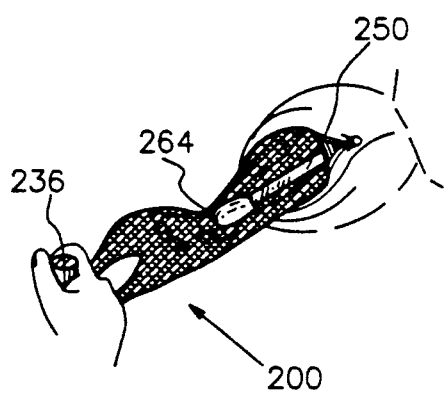
FIG. 26 is a three dimensional view of an embodiment of the invention being inserted and positioned to deliver a breech birth.
Figure 27:
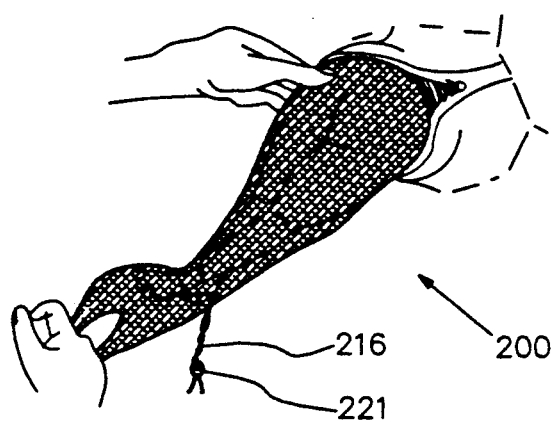
FIG. 27 is another three dimensional view of the embodiment shown in FIG. 26 being used to deliver a breech birth.

Still another embodiment of the invention is depicted in figs. 26 and 27 which depicts the device being utilized for breech births. FIG. 26 illustrates the device being inserted and positioned for the breech delivery. FIG. 27 represents the device being used to deliver the fetus.

In operation, the device 3, as shown in the embodiments of FIGS. 1–4, is first positioned on the top of the fetus' head 4 with the wands 27 fitted into pockets 25. The wands 27 are then maneuvered by pushing the ends of each wand 27 against the inside walls of their respective pocket 25 until the device is slipped over the fetus' head. When the collar 7 extends posterior to the head 4 the physician then adjusts collar 7 so that it fits loosely about neck area 10, but is restricted so as not to easily slip over the head 4. The physician then grabs the end 11 and applies a pulling force which will cause the collar 7 to exert an equalized and evenly distributed resistance to the pulling force sufficient to initiate axial uniform gripping of the fetal skull in the manner of the Chinese Handcuff. This pulling force will assist the mother in natural childbirth. Once the fetus has been removed, the physician then removes device 3 from the head 4. The device is then preferably discarded and not reused.

As regards the method of assisting the delivery of an infant during childbirth utilizing the elongated member of FIG. 5 and the insertion means of FIGS. 14A and B, first, the insertion means, which comprises of members 162, 164, and 166, are fitted into the pocket means 114. Then, the collar means 110 is guided over the infants head by applying force to the insertion means until the collar is anteriorly below chin depth and posteriorly below the smallest portion of fetal skull as shown in FIG. 13.

Next, the device is pulled from the second end 104 of the elongated member 100, and the pulling force exerted on the second end 104 will be uniformly distributed about the fetus' skull due to the axial gripping of the mesh. Continuous or intermittent pulling, as needed, on the second end 104 will result in assistance in delivery of the infant.

The delivery of the child may also be accomplished with any of the other embodiments heretofore disclosed. For instance, the insertion means 116 may be employed, instead of use of the members 162, 164, and 166, for guiding the collar means 110 over the infants head. In such a case, after the apparatus has been positioned through manipulation of the first and second members, 120 and 122, the insertion means 116 will be withdrawn as heretofore described. Also, the handle means 152 may also be employed, as previously described.

The operation of the preferred embodiment shown in FIG. 20 will now be described with reference to FIG. 23 which depicts a cut-away view of the infant in the birth canal with the device 200 being placed about the head of the fetus when the fetus is in the occipital anterior position. Generally, the device 200, and in particular end 204, is inserted at the vaginal introitus using the cephalic curve insertion wand member 250. If deemed appropriate, two insertion wand members 250 may be employed. The shrink wrap means 270 will be inserted to a suitable depth, which is generally about one-half inch to three-quarters of an inch, depending on the particular circumstances. After positioning the end 204 of device 200 to the proper depth, the tabs 272, 274 are pulled and the shrink wrap means 270 is removed and discarded.

Next, the device 200 is inserted with the wands 250 being introduced and enclosed between the layers 210, 212 (within the nylon sheath 222) in sequential fashion i.e. incrementally moving the collar means 214 below the mandible area, to the lateral aspect of the fetal head allowing the device to pass cephalad encircling the fetal head. After completion of this maneuver, the collar means 214 should be enveloping the mentum of the fetus. If two sheaths 222 are utilized, two insertion wands 250 will also be utilized, thereby allowing for incremental movement by each wand, each in separate movements.

Referring to FIG. 24, once sufficient depth of the collar means 214 has been reached by the transmitting of force from the insertion wand end 258 to the device 200, the operator will begin to pull on the drawstring 216 by grasping the fastener 221 and pulling. Concurrent with this step, the operator will also continue to place a force on the end 204 which will ensure that the collar means 214 will remain in place about the neck of the fetus. The means for transmitting this force is the insertion wand 250. Force will be applied by the operator of the device such that the end 258 is pushing the end 204 of the device since the sheath 222 is attached to the cylindrical member at 226.

Once sufficient constriction of the diameter of the collar 214 has taken place, the insertion wands 250 are then removed from the sheaths 222 separately and the operator may continue lateral pulling on the handle 236 so that axial gripping forces of the angular mesh 208 can be initiated which in turn distributes the pulling force to all areas of the mesh which have been expanded by the infant's head. If it is necessary to reposition the device, replace the wands 250 into the sheaths 222 on either side if two sheaths and two wands have been used.

Appropriate traction should be applied to the distal end 206 and handle 236 of the device 200. This will cause the angular mesh braided material 208 to axially grip the fetal head. Constant or intermittent traction can be applied to facilitate the fetal head's passage through the vaginal canal.

The invention is also applicable for use in breech births as seen in FIGS. 26 and 27. In a breech footlet presentation, the feet of the infant protrude from the introitus. In a breech delivery, the doctor will be pulling on the legs and then thighs as delivery progresses. Many times this results in injury to the skeletal growth plates of the lower extremity of the fetus. Thus, in anticipation of a breech birth, the device 200, and in particular the cylindrical member 202 is simply manufactured such that the cylindrical member 202 is longer. This is necessary because the cylindrical member will be fitted from the feet to about the hip area as illustrated in FIGS. 26 and 27.

In a breech delivery, the method includes positioning the device 200 over the leg and thigh portion of the child by manipulation of the wand 250 in sheath 222. Once sufficient penetration has occurred, the operator may begin lateral pull on the handle means 236 which will initiate axial gripping on those parts of the body that have expanded the cylindrical member 202. Continual pressure on the end 204 by the insertion wand 250 is maintained by the operator.

Movement of the fetus from the womb will allow for the relaxation of the axial gripping, and it will be necessary to further position the end 204 further up the body of the fetus to above the thigh and hip. This is accomplished in the same fashion in that the wands 250 are pushed sequentially upward until the appropriate depth is reached wherein pressure is maintained on the end 204 by the wand 250, the drawstring is tightened and the cylinder 202 is laterally pulled thereby initiating axial gripping. Thereafter, the wand can be removed and lateral pull may continue in order to deliver the fetus.

Finally, the invention should be understood to assist in the delivery of any type of fetus, and not limited to human fetus. In other words, the embodiments disclosed would also be applicable to veterinary obstetrics in deliveries of such mammals as horses, cattle, and sheep.

There are, of course, other alternate embodiments which are obvious from the foregoing descriptions of the invention which are intended to be included within the scope of the invention as defined by the following claims.

I claim:

1. An apparatus for assisting the delivery of a fetus comprising:
   an elongated member having a passageway into which the head of said fetus may be fit, said elongated member having a first end and a second end; said first end being constructed and shaped for encircling the neck of said fetus so that said first end of said elongated member surrounds said head;
   a sheath member, disposed along said elongated member, said sheath member having a terminal end and a receiving end, and wherein said terminal end is attached to the first end of said elongated member and said receiving end is attached intermediate said first end and said second end;
   insertion means capable of inserting said first end of said elongated member over said head; wherein said insertion means is adapted to be received within said receiving end of said sheath for positioning said first end over said fetal head.

2. The apparatus of claim 1 wherein said elongated member is constructed of a braided material.

3. The apparatus of claim 2 wherein said braided material comprises a first and second material, and wherein said first material is a flat shoe lace material and said second material is a series of monofilament strands.

4. The apparatus of claim 1 or 3 wherein said elongated member comprises an outer layer and an inner layer so that a double layered elongated member is formed.

5. The apparatus of claim 4 further comprising:
   collar means, attached to said first end of said elongated member, and
   tightening means positionable within said collar means for tightening said collar means about the neck of said fetus.

6. The apparatus of claim 5 wherein said tightening means comprises a draw string having a first end and a second end, and wherein said draw string is positioned within said collar means and extends at least partially about said first end of said elongated member and traverses toward said second end of said elongated member; wherein said first and second ends of said draw string are joined together at the second end of said elongated member so that as said first and second end of said draw string are pulled, said collar means is tightened about said neck of said fetus.

7. The apparatus of claim 6 further comprising handle means, attached to said second end of said elongated member, for facilitating exertion of a pulling force on said elongated member in order to initiate and maintain axial gripping of said elongated member on said head.

8. The apparatus of claim 7 further comprising removal ring means, attached to the outer layer of said elongated member, for exerting a force on said outer layer of said elongated member so that previously initiated axial gripping is reduced to permit removal of said elongated member from said head of said fetus.

9. The apparatus of claim 8 further comprising a means, attached to said first end of said elongated member, for causing said first end of said elongated member to be constricted into a diameter sufficient to allow insertion of said first end of said elongated member into the womb of the mother and allowing said first end of said elongated member to expand to a greater diameter after said first end has been sufficiently inserted into said womb of said mother.

10. A method of assisting the delivery of an infant during birth, the method comprising the steps of:
   a) preparing an apparatus for insertion into a womb of a mother, said apparatus including: an elongated member having a first and second end; sheath means attached at one end to said first end of said elongated member and at an opposite end to a position intermediate said first and second end of said elongated member for receiving an insertion member; said elongated member structured for encircling the neck of the infant so that said elongated first end of said elongated member surrounds the head of said infant and wherein a draw string means for tightening said first end of the elongated member about said neck of said infant is attached about said first end of said elongated member and extended down said elongated member past said position; a constricting means for allowing said elongated member to be compressed to a diameter sufficient for insertion into the introitus of the mother including a plastic cylindrical member with a perforated line and tabs generally aligned with the perforations;
   b) inserting said elongated member into said introitus
   c) pulling the tabs so that said constricting means separates at said perforations for removal and discarding so that said elongated member is allowed to expand;
   d) introducing an insertion member into said sheath means;
   e) guiding said first end of said elongated member over said fetal head by applying force to said insertion member so that the force is transferred to said sheath means until said first end of said elongated member is posterior to said head;
   f) continuing to apply force by said insertion member to said sheath means;
   g) tightening the draw strings so that said first end is fitted about said neck of said infant.

11. The method of claim 10 further comprising the steps of:
   pulling said apparatus at said second end so that said first end exerts an equalized and evenly distributed resistance to pulling sufficient to initiate axial gripping by said mesh of said elongated member about said head;
   removing said insertion member from said sheath means; and
   delivery of said infant.

12. The method of claim 10 further comprising the steps of:
   pulling said device at said second end so that said collar means exerts an equalized and evenly distributed resistance to pulling sufficient to initiate axial gripping by said mesh of said elongated member about the fetal head;
   pulling on removal rings attached to said elongated member in order to interrupt said axial gripping; and
   removing said elongated member before delivery of said infant.

* * * * *